United States Patent
Guo et al.

(10) Patent No.: US 12,017,056 B2
(45) Date of Patent: Jun. 25, 2024

(54) POLYMER COATINGS FOR SHAPE MEMORY ALLOYS FOR USE IN PERCUTANEOUS HEART PUMPS

(71) Applicant: TC1 LLC, St. Paul, MN (US)

(72) Inventors: Xiaoping Guo, Eden Prairie, MN (US); David Panus, Maple Grove, MN (US)

(73) Assignee: TC1 LLC, St. Paul, MN (US)

( * ) Notice: Subject to any disclaimer, the term of this patent is extended or adjusted under 35 U.S.C. 154(b) by 875 days.

(21) Appl. No.: 17/044,976

(22) PCT Filed: Mar. 18, 2019

(86) PCT No.: PCT/US2019/022749
§ 371 (c)(1),
(2) Date: Oct. 2, 2020

(87) PCT Pub. No.: WO2019/194956
PCT Pub. Date: Oct. 10, 2019

(65) Prior Publication Data
US 2021/0162200 A1   Jun. 3, 2021

Related U.S. Application Data

(60) Provisional application No. 62/652,536, filed on Apr. 4, 2018.

(51) Int. Cl.
*A61M 60/237* (2021.01)
*A61M 60/117* (2021.01)
(Continued)

(52) U.S. Cl.
CPC ........ *A61M 60/237* (2021.01); *A61M 60/117* (2021.01); *A61M 60/216* (2021.01);
(Continued)

(58) Field of Classification Search
CPC .............. A61M 60/135; A61M 60/148; A61M 60/178; A61M 60/216; A61M 60/414; A61M 60/585; A61M 60/857
See application file for complete search history.

(56) References Cited

U.S. PATENT DOCUMENTS 6,013,855 A   1/2000   McPherson
6,017,577 A   1/2000   Hostettler et al.
(Continued)

FOREIGN PATENT DOCUMENTS

WO   2016202574 A1   12/2016

OTHER PUBLICATIONS

Babu et al: "Biostability of Thoralon Left Ventricular Assist Device Blood Pumping Sacs After Long-Term Clinical Use :", Asaio Journal., vol. 50, No. 5, Sep. 1, 2004 (Sep. 1, 2004), pp. 479-484, XP055594996, US ISSN: 1058-2916, DOI: 10.1097/01.MAT. 0000136511.99220.8B.
(Continued)

*Primary Examiner* — Jon C Morales
(74) *Attorney, Agent, or Firm* — Armstrong Teasdale LLP

(57) ABSTRACT

The present disclosure relates generally to percutaneous heart pumps including a self-expandable and collapsible impeller housing fabricated from a mesh of a shape memory alloy, such as nitinol, and a base polymer coating and a top polymer coating. Specifically, the present disclosure relates to highly flexible and fluid-impermissible polymer coatings having improved adherence and performance properties on the metallic surfaces of the impeller housing mesh thus improving the overall performance of the percutaneous heart pumps.

21 Claims, 7 Drawing Sheets

(51) Int. Cl.
   *A61M 60/216*    (2021.01)
   *A61M 60/81*     (2021.01)
   *C09D 175/04*    (2006.01)
   *C09D 183/06*    (2006.01)
   *C23C 18/04*     (2006.01)
   *C23C 18/12*     (2006.01)

(52) U.S. Cl.
   CPC ........... *A61M 60/81* (2021.01); *C09D 175/04* (2013.01); *C09D 183/06* (2013.01); *C23C 18/04* (2013.01); *C23C 18/122* (2013.01); *C23C 18/1241* (2013.01); *A61M 2205/0238* (2013.01); *A61M 2205/0266* (2013.01)

(56) References Cited

U.S. PATENT DOCUMENTS

| | | |
|---|---|---|
| 2009/0169714 A1 | 7/2009 | Burghard |
| 2013/0331639 A1 | 12/2013 | Campbell |
| 2014/0012065 A1 | 1/2014 | Fitzgerald |
| 2019/0290817 A1* | 9/2019 | Guo .................. A61M 60/414 |

OTHER PUBLICATIONS

Adhikari et al, "Biodegraable Polyurethaes: Design, synthesis, Properties and Potential,", Jan. 1, 2011 (Jan. 1, 2011), 54 pages, XP055595085, Retrieved from the Internet: URL: https://www.researchgate.net/publication/234027642_Biodegradable_Polyurethanes_Design_Synthesis_Properties_and_Potential.

Written Opinion of the International Searching Authority for International Application No. PCT/US2019/022749, dated Sep. 23, 2019, 17 pages.

* cited by examiner

HYDROLYSIS
CONDENSATION
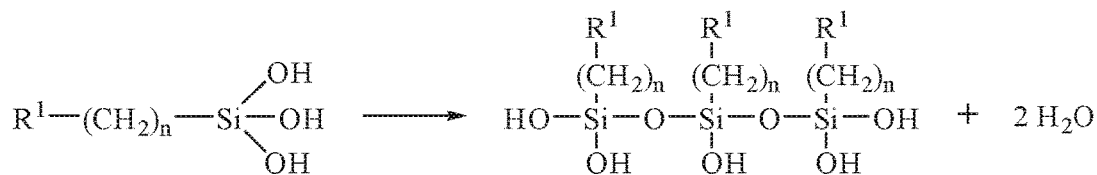
FIG. 4
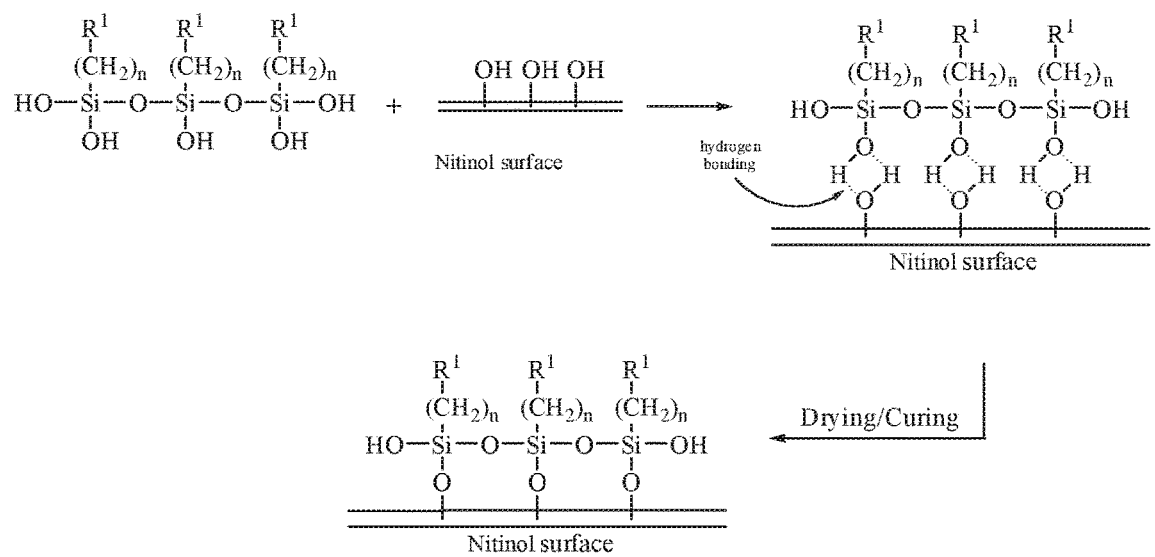
FIG. 5

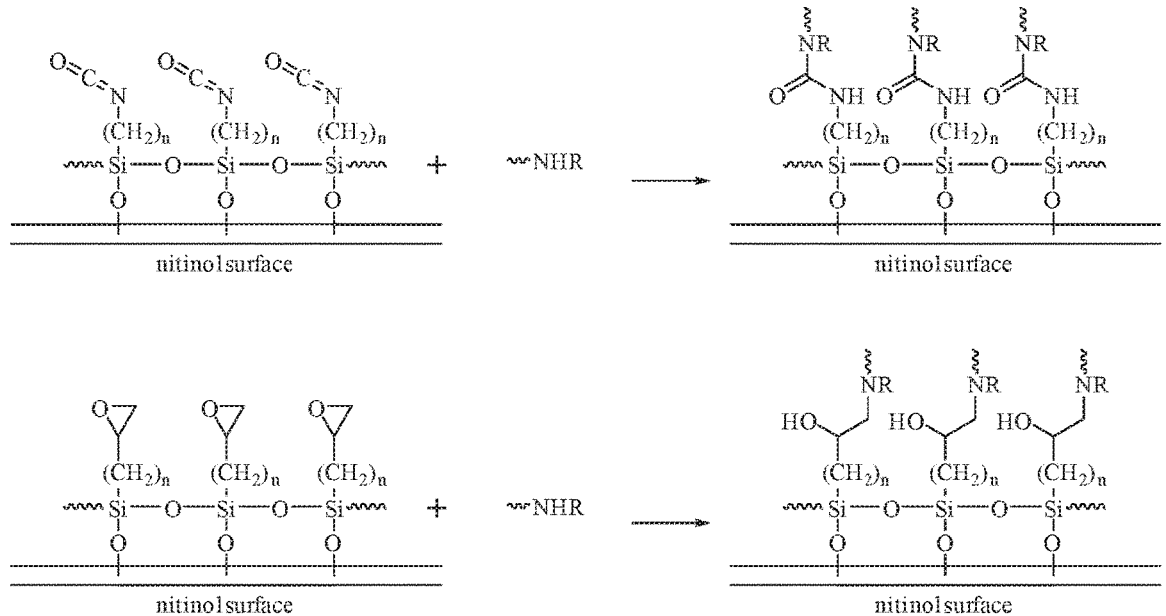

where the ~~NHR represents an amino/amine reactant added to a base or top coating or a biocompatible polymer comprising the top coating when a single organosilane compound having an oxirane or isocyanate group is used for the base coating.

FIG. 6A

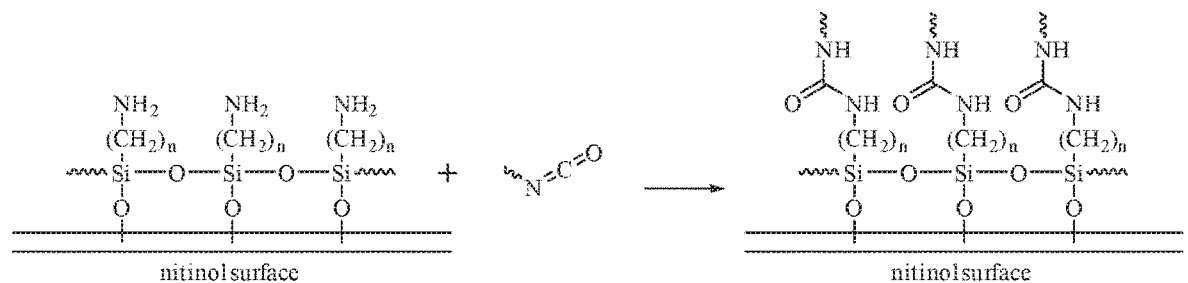

where the ~~N=C=O represents a liquid isocyanate reactant added to the base or top coating when a single organosilane compound having an amine functional group is used for the base coating.

FIG. 6B where ~~~<O represents a liquid epoxy reactant added to the base or top coating when a single organosilane compound having an amine functional group is used for a base coating.

POLYMER COATINGS FOR SHAPE MEMORY ALLOYS FOR USE IN PERCUTANEOUS HEART PUMPS

CROSS REFERENCE TO RELATED APPLICATIONS

This application is a national stage entry of PCT/US2019/022749, filed Mar. 18, 2019, which claims priority to provisional application Ser. No. 62/652,536, filed Apr. 4, 2018, which are both incorporated herein in theft entirety.

BACKGROUND OF THE DISCLOSURE a. Field of the Disclosure

The present disclosure relates generally to percutaneous heart pumps including a self-expandable and collapsible impeller housing fabricated from a shape memory alloy, such as nitinol, a base coating, and a top coating. More specifically, the present disclosure relates to highly flexible and fluid-impermissible integral base and top polymer coatings having improved adherence and performance properties on the interior and exterior surfaces of the impeller housing in a percutaneous heart pump thus improving the overall performance of the impeller housing.

b. Background Art

Heart disease is a major health problem that claims many lives per year. After a heart attack or other major cardiac event, only a small number of patients can be treated with medicines or other non-invasive treatment. A significant number of patients, however, can recover from a heart attack or other cardiac event if provided with mechanical circulatory support in a timely manner.

In one conventional approach for treating patients, a blood pump having a fixed cross-section is surgically inserted into a heart chamber, such as into the left ventricle of the heart and the aortic arch, to assist the pumping function of the heart. Other known conventional applications involve providing for pumping venous blood from the right ventricle to the pulmonary artery for support of the right side of the heart. The object of the surgically inserted pump is to reduce the load on the heart muscle for a period of time, which may be as long as a week, allowing the affected heart muscle to recover and heal. In some cases, surgical insertion may potentially cause additional stresses in heart failure patients.

In many cases, percutaneous insertion of a left ventricular assist device ("LVAD"), a right ventricular assist device ("RVAD"), or in some cases a percutaneous system for both sides of the heart (sometimes called biVAD) is a desirable alternative. The pump component of the device includes an impeller encased in a housing, while blood, driven by the impeller, traverses the interior of the housing. Impedance of the blood flow can potentially cause hemolysis of red blood cells and have a potentially negative effect on the patient outcome. In some cases, conventional fixed cross-section ventricular assist devices designed to provide near full heart flow rate may be too large to be advanced percutaneously, e.g., through the femoral artery.

During percutaneous insertion and use of the heart pump, it is desirable that the lubricity and integrity of the surfaces of the pump that are exposed to the patient vasculature be maximized. This maximization of the lubricity and integrity reduces the potential for blood hemolysis and irritation at the intravascular location of the pump. Improving the lubricity of the surfaces in such devices that interact with the vasculature of a patient (e.g., the blood or the blood vessels) will improve their effectiveness and further improve patient outcomes.

SUMMARY OF THE DISCLOSURE

The present disclosure is directed to an impeller assembly for a heart pump. The impeller assembly comprises: (i) an impeller shaft; (ii) an impeller blade extending from the impeller shaft; (iii) an impeller housing in which the impeller shaft is journaled for rotation, wherein the impeller housing comprises a metallic mesh and includes an impeller blade zone, an inlet zone, an outlet zone, and an elongate wall structure; and (iv) a polymer coating on the metallic mesh, the polymer coating comprising a base coating that is in direct contact with the metallic mesh and a top coating that is in direct contact with the base coating, wherein the top coating is integral with the base coating and itself to thereby render the elongate wall structure fluid-impermissible.

The present disclosure is further directed to a method of a preparing a coated substrate. The method comprises: (i) applying a cleaning solution to a substrate to prepare a cleaned substrate, wherein the substrate comprises a shape memory alloy; (ii) applying a first coating solution to the cleaned substrate, wherein the first coating solution comprises a multifunctional organosilane compound that comprises at least two functional groups that are converted to silanol groups upon reaction with water, and at least one functional group selected from the group consisting of amines, isocyanates, and oxiranes; (iii) rinsing the substrate with a solvent thereby making a rinsed substrate; (iv) curing the rinsed substrate thereby making a base coated substrate; (v) applying a second coating solution to the base coated substrate, wherein the second coating solution comprises a biocompatible polymer resin, blend, or compound; and (vi) curing the substrate thereby making the coated substrate.

BRIEF DESCRIPTION OF THE DRAWINGS

FIG. 4 illustrates hydrolysis and condensation of a multifunctional organosilane coupling compound used to prepare some embodiments of a base coating.

FIG. 5 illustrates one embodiment of the formation of a base coating on a shape memory alloy.

FIGS. 6A, 6B and 6C illustrate exemplary embodiments of a top coating layer adhered to a base coating. 6A illustrates isocyanate and oxirane functional groups of a base coating adhered to an amine group in a top coating, respectively. 6B illustrates an amine or amino functional group of a base coating adhered to an isocyanate group in a top coating. 6C illustrates an amine or amino functional group of a base coating adhered to an oxirane group in a top coating.

DETAILED DESCRIPTION OF THE DISCLOSURE

Percutaneous heart pumps and components therefor of the present disclosure can be used to treat individuals experiencing cardiac stress, including acute heart failure. The percutaneous heart pumps described herein include one or more components that include a highly stable polymeric coating thereon that reduces overall friction and increases lubricity. This may lead to better and more consistent blood flow with decreased blood hemolysis through the device and an improved sleekness for the advancement and retraction of the relevant delivery catheter system. The polymeric coatings described herein are integral with one another and include multiple layers and attach securely to a metallic mesh that forms the impeller housing for the percutaneous heart pump thereby resulting in an improved overall performance with a decreased incidence of delamination of the coating during use.

In many embodiments of the present disclosure, the surfaces of the impeller housing, which is self-expandable and collapsible and generally fabricated from a laser-cut or braided shape memory alloy mesh and surrounds the impeller as discussed in more detail herein, include an integral combination of a base coating and a top coating that renders the impeller housing circumferentially fluid-impermissible; that is, the coated impeller housing (metallic mesh) does not allow blood (or any other fluid) to permeate its interior and exterior surfaces. These integral coatings have improved polymer adherence to the shape memory alloy mesh and provide other advantages discussed herein. The polymeric coatings described herein generally provide a base coating formulation comprising one or more specialty multifunctional organosilane coupling compounds and other compounds, which form a thin siloxane polymer film, or siloxane monolayer directly on the metallic surfaces of the mesh of a shape memory alloy. When this thin film or monolayer is dried and cured as described herein, it provides strong covalent bondability and adhesion to the metallic mesh and some active molecular mechanism of adherence to another top layer, such as a top coating, that may be applied onto the base coating. The top coating as described herein provides a flexible, and integral fluid-impermissible film circumferentially encapsulating the impeller housing formed from the metallic mesh. Both the base coating and the top coating as described herein may be present on the coated substrate in one or more layers. Although discussed primarily herein in combination with a coating on an impeller housing formed from a shape memory alloy metallic mesh, it should be recognized that it is within the scope of the present disclosure for other components of the percutaneous heart pumps described herein to include the polymer coatings of the present disclosure.

a. Heart Pump System Overview

Figure 1:
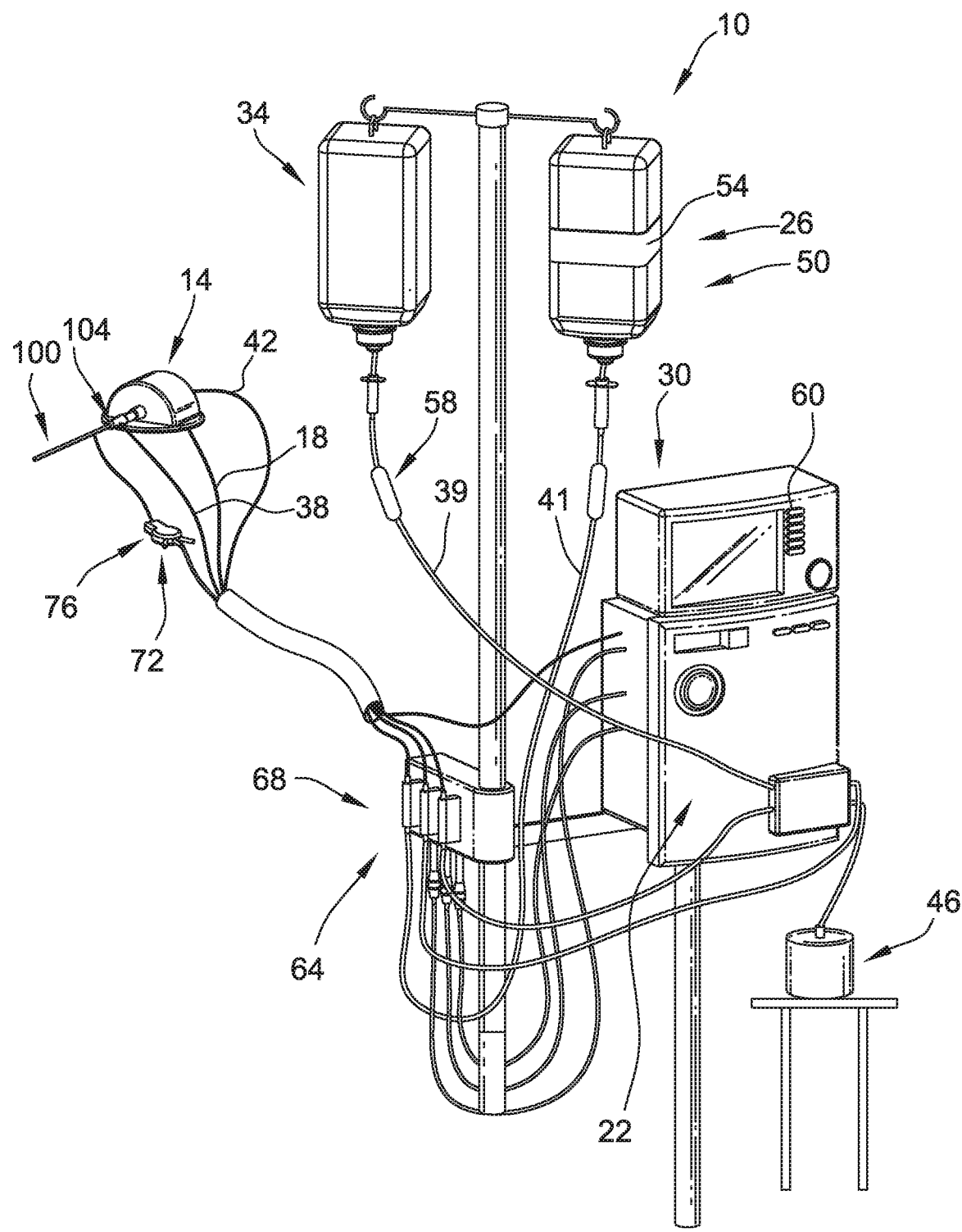
FIG. 1 illustrates one embodiment of a percutaneous heart pump configured for percutaneous application and operation.
Figure 2:
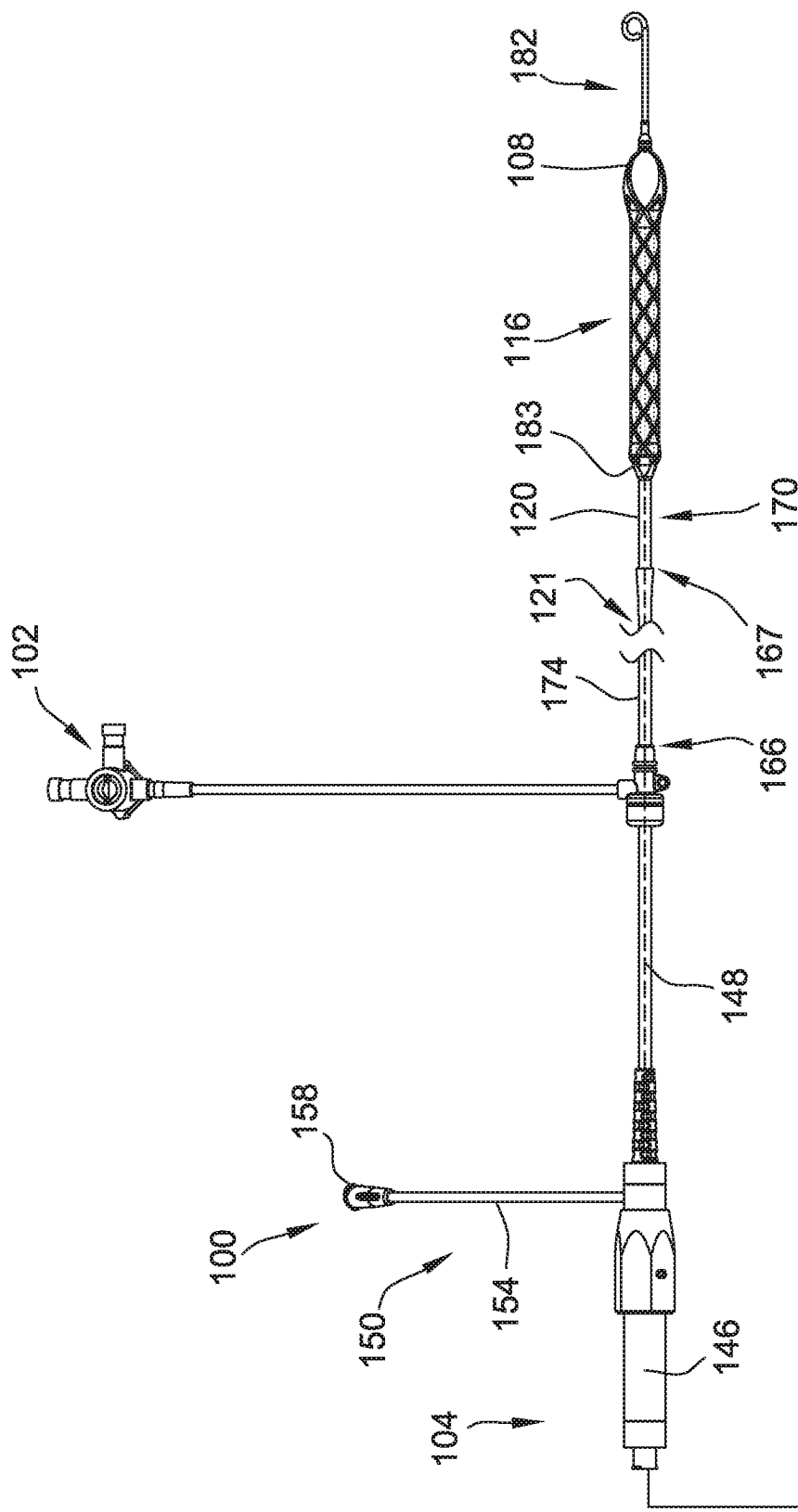
FIG. 2 is a plan view of one embodiment of a catheter assembly adapted to be used with a percutaneous heart pump.

Referring now to the Figures, and specifically to FIG. 1, there is illustrated one embodiment of a heart pump 10 that includes a catheter assembly 100 having a proximal end 104 adapted to connect to a motor 14 and a distal end 108 (as shown in FIG. 2) adapted to be inserted percutaneously into a patient (not shown in FIG. 1). Motor 14 is connected by a signal line 18 to a control module 22 that provides power and/or control signals to motor 14. Heart pump 10 may have an infusion system 26 and a patient monitoring system 30.

Infusion system 26 can provide a number of benefits to heart pump 10. In one embodiment, infusion system 26 includes a source of infusant 34, a fluid conduit 38 extending from infusant source 34 to proximal end 104 of catheter assembly 100 and a fluid conduit 42 extending from proximal end 104 of catheter assembly 100 to a waste container 46. The flow of an infusant to and from catheter assembly 100 can be by any means, including a gravity system or one or more pumps. In FIG. 1, infusant source 34 includes an elevated container 50 and fluid conduit 41, which may be saline or another infusant as necessary based on patient requirements. Flow from elevated container 50 through fluid conduit 39 can be regulated by a pressure cuff 54 to elevate the pressure of the fluid in container 50 to increase flow or by a pinch valve 58 or by other means.

With continuing reference to FIG. 1, patient monitoring system 30 can be used to monitor the operation of the patient and/or pump 10. For example, patient monitoring system 30 can include a user interface 60 coupled with a source of data 64. Data source 64 can include one or more patient condition sensors, such as pressure sensors 68 that are in pressure communication with the patient and/or operating components within the patient. In one embodiment, pressure sensors 68 fluidly communicate by a conduit 72 that extends between the sensors and a proximal portion of catheter assembly 100. Conduit 72 can include a plurality of separable segments and can include a valve 76 to enable or disable the pressure communication to sensors 68.

Heart pump 10 is adapted to provide an acute or other short-term treatment. A short-term treatment can be for less than a day or up to several days or weeks in some cases. With certain configurations pump 10 can be used for a month or more.

FIG. 2 illustrates one embodiment of a catheter assembly to be used with the heart pump 10 (see FIG. 1). An impeller housing 116 disposed at distal end 108 is configured to pump blood proximally or distally through or along a portion of heart pump 10 to convey blood from one body cavity to another. Impeller housing 116 can be arranged to pump blood distally, such as in a right heart assist mode to move blood from the right ventricle to the pulmonary artery. Proximal flow is optimal for left heart support to move blood from the left ventricle to the aorta. Heart pump 10 can be used to treat patients with acute heart failure, ST elevation myocardial infarction (STEMI), cardiac arrest, cardiac arrhythmia or other heart maladies as noted above. Heart pump 10 also can be used in connection with a surgical treatment to support the patient without providing full cardiovascular bypass. A patient could be supported on the device for longer term with proper controls and design.

One feature that facilitates percutaneous insertion is providing catheter assembly 100 with a low profile configuration. For example, distal end 108 of catheter assembly 100 can be configured to have about an 11 French (approximately 3.5 mm) size in a first configuration for insertion and an expanded configuration, such as up to about 21 French (approximately 7 mm) once in place in the body. The larger size facilitates greater flow rates by impeller housing 116. Of course, other sizes for insertion and expansion are within the scope of the present disclosure.

Catheter assembly 100 is configured to enable distal end 108 to reach a heart chamber after being inserted initially into a peripheral vessel. For example, catheter assembly 100 can have a suitable length to reach the left ventricle and sufficient pushability and torquability to traverse the intervening vasculature. Catheter assembly 100 may include an inner sheath assembly 170 including a multilumen elongate inner sheath body 120 that is arranged to distally dispose an impeller housing 116. Catheter assembly 100 may further include an outer sheath assembly 121 that is arranged to facilitate the delivery and operation of heart pump 10 including the collapsible and self-expandable impeller housing 116. Further details concerning various embodiments of catheter assembly 100 are described in more detail in U.S. Pat. No. 8,597,170.

A drive system is provided to drive an impeller 165 (see FIG. 3) encased within impeller housing 116. The drive system includes motor 14 and a drive controller, which can be integrated into control module 22 (see FIG. 1). Although motor 14 may be configured to be disposed outside the patient, some structures and assemblies described herein could be incorporated into a system in which a motor is miniaturized sufficiently to be inserted into the patient in use, including into the vasculature.

Figure 3:
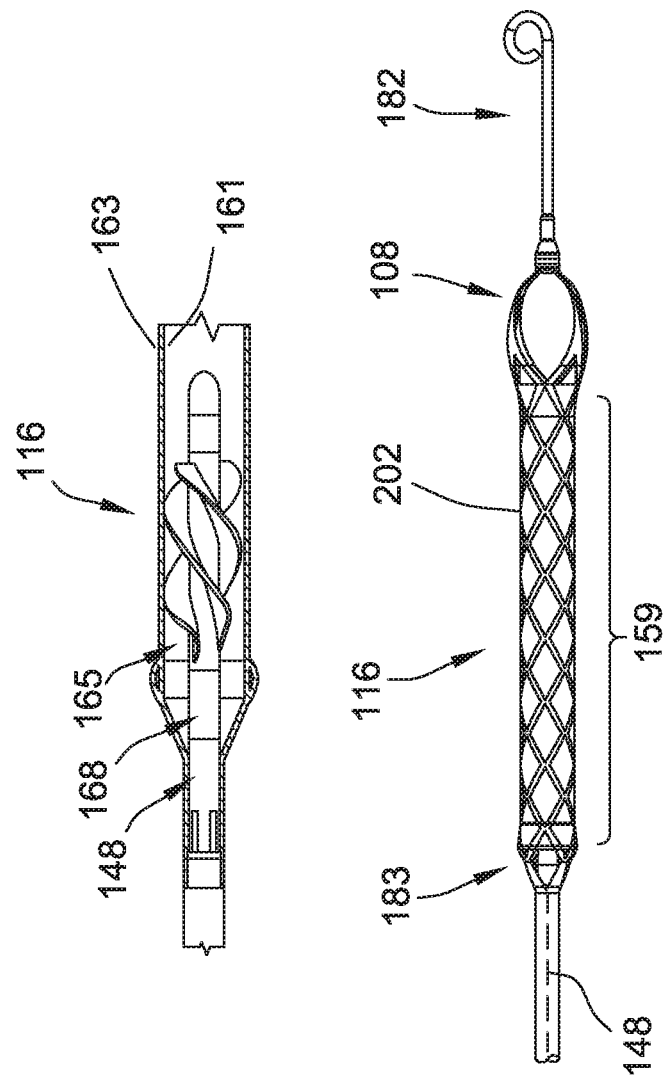
FIG. 3 is one embodiment of an impeller assembly for use in a percutaneous heart pump.

A torque coupling system is provided for transferring torque from motor 14 to impeller shaft 168 (see FIG. 3). The torque coupling system is discussed further in U.S. Pat. No. 8,597,170, but in general can include a mechanical or magnetic interface disposed between motor 14 and a drive assembly that is disposed at proximal end 104 of catheter assembly 100. The drive assembly is coupled with a proximal end of an elongate flexible drive cable 148 in one embodiment. The elongate flexible drive cable 148 extends from drive assembly 146 through the center lumen of inner sheath body 120, and is then distally coupled with impeller shaft 168 that resides inside impeller housing 116.

FIG. 2 shows an infusion inflow assembly 150 that can form a part of infusion system 26 (see FIG. 1). The infusion in assembly 150 is provided adjacent proximal end 104 in one embodiment. Infusion system 26 is configured to convey one or more fluids therein in connection with operation of impeller housing 116 or the conducting of the treatment. In one embodiment, an infusant, e.g., a medication or a lubricating fluid, such as saline or other beneficial medium, is conveyed distally along the pump, e.g., within multilumen inner sheath catheter body 120, toward the operating components adjacent to distal end 108. The infusant can include lubrication fluids such as glucose or other biocompatible lubricants. Infusion inflow assembly 150 includes an extension tube 154 having a luer or other suitable connector 158 disposed at a proximal end thereof and an inflow port in fluid communication with one or more lumens within catheter assembly 100 or specifically, inner sheath assembly 170. A lumen extending through extension tube 154 is adapted to be fluidly coupled with a fluid source connected to connector 158, to deliver the fluid into catheter assembly 100 and through one or more flow paths.

FIGS. 2 and 3 illustrate housing mesh 202 disposed at distal end 108. Housing mesh 202 forms an elongate structure 159 having a distal end 108 and a proximal end 183 and elongate structure 159 is encapsulated by flexible polymer coatings to form impeller housing 116 in that it houses an impeller 165 (connected to impeller shaft 168) and provides clearance against the impeller to prevent any harmful interactions therebetween. Impeller housing 116 and impeller 165 are also carefully integrated to maintain an appropriate flow regime, e.g., from distal to proximal within the housing. FIG. 3 shows that in some embodiments housing mesh 202 is a mesh structure of filaments that extend axially and wrap circumferentially around a central axis. Housing mesh 202 can take any suitable form, such as being constructed to prevent kinking upon delivery or to control the spacing between a radially outer edge of an impeller and an impeller housing that comprises an elongate mesh structure (e.g., elongate structure 159) and a polymer coating (as described herein). In some embodiments, housing mesh 202 is a laser cut metallic strut comprising a shape memory alloy.

Catheter assembly 100 can include an outer sheath assembly 121 around inner sheath assembly 170 and configured to constrain impeller housing 116 in a low profile configuration in a first state and to permit impeller housing 116 to expand to the enlarged configuration in a second state. Outer sheath assembly 121 has a proximal end 166, a distal end 167, and an elongate sheath body 174 extending therebetween. Elongate sheath body 174 has a lumen extending between the proximal end 166 and distal end 167. Outer sheath assembly 121 provides a passageway for inner sheath assembly 170 to be sleekly disposed through outer sheath assembly 121. The arrangement permits outer sheath assembly 121 to be positioned between an advanced position corresponding to the low profile configuration and a retracted position corresponding to the enlarged configuration. In some embodiments, a luer 102 or other suitable connector is in fluid communication with proximal end 166 of outer sheath assembly 121. Luer 102 can be configured to deliver fluids to catheter assembly 100, such as priming fluid, infusant, or any other suitable fluid.

FIGS. 2 and 3 also show that distal end 108 of catheter assembly 100 includes impeller housing 116 and atraumatic tip 182 disposed distal of impeller housing 116. Atraumatic tip 182 can have an arcuate configuration such that interactions with a patient's internal tissues are controlled and do not cause trauma thereto. Atraumatic tip 182 can take any suitable shape, which can vary depending on the degree of curvature of the tip. The tip is designed to be atraumatic so that after retraction of the guidewire, when the tip is left inside, for example, a ventricle, it cannot cause injury or trauma to the inner wall or endocardial surface of the ventricle resulting from motion of the ventricle.

Atraumatic tip 182 can include a 180° bend, wherein the distal-most end of atraumatic tip 182 is generally parallel to the non-arcuate portion of atraumatic tip 182, but extending in the opposite direction (e.g., a j-tip). The distal-most end of atraumatic tip 182 can be generally perpendicular to the non-arcuate portion of atraumatic tip 182, or at an angle between about 90° and about 180°. In yet another aspect, the distal-most end of atraumatic tip 182 can include a 360° bend, wherein the distal-most end of atraumatic tip 182 is generally parallel to the non-arcuate portion of atraumatic tip 182, while extending in generally the same direction. In some embodiments, the arcuate portion of atraumatic tip 182 can be coiled greater than 360°.

In some embodiments, impeller housing 116 comprises a metallic, housing mesh 202. At least a portion of housing mesh 202 is formed from a shape memory alloy exhibiting superelasticity or shape memory effect upon mechanical stimulus at body temperature (37° C.). For example, a suitable material will permit housing mesh 202 to expand from a collapsed or compressed state within the transverse profile of the sheath to an expanded state when outer sheath assembly 121 retracts proximally with respect to inner sheath assembly 170 to release impeller housing 116 from compressive restraints. Shape memory materials can also include materials capable of reversibly deforming and/or changing shape in response to a temperature change. Examples of suitable shape memory alloys include, but are not limited to, nickel-titanium (nitinol), copper-zinc, copper-zinc-aluminum, copper-aluminum-nickel, and gold-cadmium. In some embodiments, at least a portion of housing mesh 202 can be formed from nitinol. In one desirable embodiment, essentially the entire housing mesh 202 for impeller housing 116 can be formed from nitinol. In other embodiments, other shape memory alloys, such as shape memory polymers and/or ceramics, can be used. In yet other embodiments, at least a portion of housing mesh 202 may not be formed from a shape memory alloy. For example, in some embodiments, at least a portion of housing mesh 202 can be formed from stainless steel. Housing mesh 202 can comprise commercially available materials that provide suitable collapsibility or expandability.

b. Impeller Housing Coating on Inner and/or Outer Surfaces

Impeller housing 116 as shown in FIG. 3 discussed above is comprised of housing mesh 202 generally constructed of nitinol and flexible, polymer coatings providing an elongate fluid-impermissible wall that circumferentially encapsulates housing mesh 202 in many embodiments and interacts directly with the vasculature of a patient. An inner surface 161 of impeller housing 116 is in direct physical contact with the blood while an outer surface 163 of impeller housing 116 is in contact with the blood vessel into which the heart pump is inserted. As such, the nature of the coating or coatings on inner surface 161 and outer surface 163 of impeller housing 116 may impact product performance and patient outcome. The applied coatings are desirably compatible with each aspect of the patient vasculature to which it interacts, including, but not limited to, the blood and blood vessels; they should be stable during both insertion and removal of the heart pump; they should maintain their physical and chemical integrity while inserted in the patient; they should resist delamination of the applied coating from the substrate of housing mesh 202; and they should not impede blood flow during use or unnecessarily irritate the blood vessel where used.

The surface energy of nitinol (and many other shape memory alloys) is generally much higher than, or in a severe mismatch with, typical polymeric materials used in polymer solution coatings. Because of the hydrophilic nature of the surfaces of a nitinol alloy, a base coat as described herein at a submicron or monolayer level may be introduced onto the nitinol surfaces of housing mesh 202 based on a multifunctional molecule that can chemically bridge the nitinol surfaces that have a very high surface energy with a subsequent coating of a polymer material having a relatively low surface energy. This process improves the wettability of the polymer coating on the base-coated nitinol surfaces such that it enhances the final adherence of a polymeric top coating. By properly selecting the multifunctional coupling compound as described in detail herein, its relevant functional groups can provide a coupling reaction or other molecular mechanism such that covalent bonding and/or other molecular forces are present between the base coating and the top polymeric coating and also between the nitinol surface and the base coating to provide an improved nitinol-coated article without potential risk of coating delamination.

In some aspects, the base coating applied to the nitinol (or other shape memory alloy or the like) has a thickness of less than 500 μm, less than 400 μm, less than 300 μm, less than 200 μm, less than 100 μm, or even less than 50 μm. In some aspects the base coating is a monolayer.

In accordance with the above, it has been found that an improved polymer coating suitable for use in making the flexible, fluid-impermissible wall structure that circumferentially encapsulates the housing mesh can be prepared in a two-step process. First, a base coating is applied to the housing mesh, dried and cured. After curing the base coating, a top coating is applied onto the base coat-coated housing mesh and cured, one or more times, to create an integral, fluid-impermissible polymer film that fully encapsulates the base-coated housing mesh.

The base coating is formed by applying one or more multifunctional organosilane coupling compounds to the substrate (namely housing mesh or other medical device component generally formed from a shape memory alloy) to be coated. The multifunctional coupling compound comprises at least two functional groups that will convert to highly reactive silanol groups upon reaction with water, and at least one functional group selected from the group consisting of amines, isocyanates, oxiranes and combinations thereof.

In some embodiments, the multifunctional coupling compound is an organosilane coupling compound or an organosilane. Organosilanes may have only one silicon atom (Formula (I)) or they may have two silicon atoms (Formula (II)). In some aspects, two or more multifunctional organosilane coupling compounds are used in the base coating. Suitable organosilanes include those of Formula (I) and Formula (II),

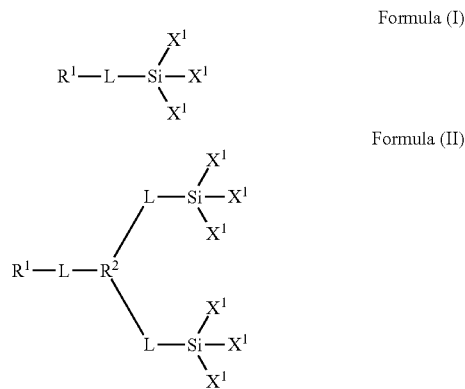

wherein each $X^1$ is independently selected from the group consisting of hydrogen, hydroxy (—OH), alkoxy (—$OR^3$), acyloxy (—$OCOR^3$), oxime (—O—N=$C(R^3)_2$), amine (—$N(R^3)_2$), and oxirane; $R^1$ is selected from the group consisting of hydrogen, —$N(R^3)_2$, isocyanate and oxirane; each L is a spacing group independently selected from the group consisting of a bond and $(CH_2)_n$; n is a number of from 1 to 20; $R^2$ is selected from the group consisting of a bond, an amine/amino, and $(CH_2)_n$ where one of the H atoms on a methylene is replaced with the -L-$R^1$ group; and each $R^3$ is independently selected from the group consisting of hydrogen and an alkyl group comprising a $C_1$ to $C_{10}$ straight or branched hydrocarbon chain.

In some aspects, the multifunctional organosilane coupling compound is a compound of Formula (I). In yet another aspect, the multifunctional organosilane coupling compound is a compound of Formula (II). In some aspects n is 1, 2, 3, 4, 5, 6, 7, 8, 9, 10, 11, 12, 13, 14, 15, 16, 17, 18, 19 or 20.

In some embodiments, two or more multifunctional organosilane coupling compounds are used. The two or more multifunctional organosilane compounds are used in any ratio that is found to improve the adherence of the top coating to the surface of the substrate. In some aspects, two multifunctional coupling compounds are used. In some other aspects, three multifunctional coupling compounds are used. In still other aspects where two multifunctional organosilane coupling compound are used, one organosilane of Formula (I) and one organosilane of Formula (II) are combined to prepare the base coating. In yet another aspect, two compounds of Formula (I) are combined to form the base coating; while in still yet another aspect, two compounds of Formula (II) are combined to form the base coating. In still yet another aspect, three compounds of Formula (I) and/or Formula (II) are combined to form the base coating. The multifunctional organosilane coupling compound has a functional group selected from an amine, an isocyanate or an oxirane (epoxide) (the $R^1$ group). In some aspects where two or more multifunctional organosilane coupling compounds are used, each compound is independently selected without regards to the other two. As such, pairs of multifunctional organosilane coupling compounds may have the same or different functional groups selected from the group consisting of amine/amino, oxirane, isocyanate and combinations thereof. By way of example and not limitation, if one organosilane compound having an amine/amino group is used in conjunction with an organosilane having either an isocyanate or epoxy group, the mole ratio of the two coupling compounds should be from 10:1 to 1:10 and all values in between. Desirably, the organosilane compounds having an amine/amino group would have a small molar excess over the compound having an isocyanate or epoxide. Small in this instance means that the molar excess would be less than 25%.

Examples of amine-containing organosilane coupling compounds used for formulating a base coating include, but are not limited to, 3-aminopropyltriethoxysilane, 3-aminopropyltrimethoxysilane, 4-aminobutyltriethoxysilane, 4-amino-3,3-dimethylbutyltrimethoxysilane, N-(2-aminoethyl)-3-aminopropyltriethoxysilane, N-(2-aminoethyl)-3-aminopropyltrimethoxysilane, N-(6-aminohexyl)aminomethyltrimethoxysilane, N-(6-aminohexyl)aminomethyltriethoxysilane, and N-(α-aminoethy)-3-aminopropylsilanetriol, and combinations thereof.

Examples of isocyanate-containing organosilane coupling compounds used for formulating a base coating include, but are not limited to, 3-isocyanatopropyltrimethoxysilane, 3-isocyanatopropyltriethoxysilane, 3-isocyanatopropylmethyldimethoxysilane, and 3-isocyanatopropylmethyldiethoxysilane, and combinations thereof.

Examples of oxirane-containing silane coupling compounds used for formulating a base coating include, but are not limited to, (3-glycidoxypropyl)trimethoxysilane, (3-glycidoxypropyl)triethoxysilane, 5,6-epoxyhexyltriethoxysilane, (3-glycidoxypropyl)methyldimethoxysilane, (3-glycidoxypropyl)methyldiethoxysilane, (3-glycidoxypropyl)dimethylmethoxysilane, and (3-glycidoxypropyl)dimethylethoxysilane, and combinations thereof.

The solvent(s) used for preparing a base coating solution comprising one or more organosilane coupling compound(s) is selected from volatile alcohols such as methanol, ethanol, isopropyl alcohol and the like with a small amount of water at the ratio of 100:0.5 to 100:5 or 100:1 to 100:2. The concentration of the organosilane coupling compound(s) for the base coating solution altogether may vary from 0.5 to 10% (v/v) or from 1 to 5% (v/v).

Figure 6C:
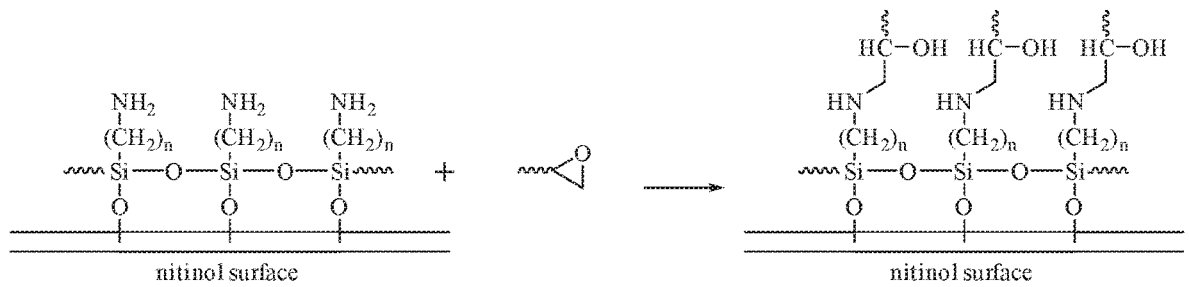

When organosilane coupling compounds having an isocyanate or an oxirane moiety are selected for preparing a base coating solution, a small amount of a commercially-available liquid amine or amino reactant in monomeric or oligomeric form, such as diethylenetriamine and/or Jeffamine® D-230, aliphatic amines, aromatic amines, polyamines, etc., may be added to the base coating solution. In some aspects, the same liquid amine reactant can be added to a top coating instead. When added to either of the top coating or the base coating, the amine reactant reacts with an isocyanate or epoxy functional group of the organosilane coupling compound(s) to create an interconnecting polymer network comprised of various polyurea or amine-rich polymeric species on the coated substrate surfaces. This imparts an inherent bondability and adherence onto the top coating which is primarily comprised of a polar polymer, such as a biocompatible thermoplastic polyurethane or a thermoplastic polyurethane/urea resin. FIGS. 6A, 6B and 6C more specifically illustrate some non-limiting embodiments of the disclosure. FIG. 6A illustrates the relevant reaction mechanism for the formation of the polyurea or amine-rich or hydroxyl-rich polymeric species on the base coated metallic substrate.

When organosilane coupling compounds having amine or amino group(s) are selected for preparing a base coating, a small amount of a commercially available liquid isocyanate reactant in monomeric or polymeric form can be added to the top coating, or, in some embodiments, to the base coating. Examples of such liquid isocyanate reactants include a urethane prepolymer derived from the polyaddition product of an isocyanate and a polyhydroxyl compound. Examples include, but are not limited to, Steralloy® series aliphatic polyurethane prepolymers like Steralloy® 2791A, Isonate® series aromatic polyurethane prepolymers like Isonate 181, and combinations thereof. FIG. 6B illustrates the proposed reaction mechanism for the formation of some polyurea or amine-rich species on the base coated metallic substrate.

In yet another aspect, when organosilane coupling compounds having amine or amino group(s) are selected for preparing a base coating, a small amount of a commercially available liquid epoxy reactant or resin can be added to the top coating, or, in some embodiments, to the base coating. Examples of such a liquid epoxy reactant include, but are not limited to, glycidyl ether(s) of aliphatic or aromatic polyglycol(s) sold as liquid epoxy diluents or resins including, but not limited to, Araldite® 506, D.E.R.™ 321, D.E.R.™ 324, etc. FIG. 6C illustrates the proposed reaction mechanism for the formation of the amino- and hydroxyl-rich polymeric species on the base coated metallic substrate. Again, it is thought that this would impart improved adherence of the base-coated substrate with the top coating via enhanced intermolecular hydrogen bonding and some covalent bonding possibly arising from the thermal curing of the base coating, and/or the top coating, and/or both.

Without being bound by any specific theory as to how the base coating attaches to the substrate surface, in some embodiments, it is believed that when a highly diluted base coating solution containing one or more organosilane coupling compound is prepared by using some volatile alcohol solvent with a small amount of water, the hydrolysis of the organosilane coupling compound spontaneously occurs within the solution, leading to the formation of highly reactive hydroxysilane or silanol. When the base coating solution is applied to the substrate, these silanols, upon physical evaporation of volatile alcohol solvent, cure via polycondensation under ambient conditions, or, in some aspects, at elevated temperature from 30 to 120° C. for some time. This leads to the formation of some oligomeric siloxane species. Such hydrolysis and condensation curing of an organosilane coupling compound are known in the art and illustrated in FIG. 4. At the same time, the silanol and oligomeric siloxane species of the base coating can concomitantly react with the metallic hydroxide present on the substrate surface via a similar polycondensation mechanism with the concomitant loss of water. This leads to the formation of a crosslinked silicone polymer film material interlocked or tightly bound to the substrate, as shown in FIG. 5. The base coating, after curing, comprises the crosslinked silicone polymer material having a functional group (R') and/or amine-rich and/or hydroxyl-rich and/or polyurea-rich species that imparts an enhanced molecular mechanism of adherence to the top coating via intermolecular hydrogen and/or covalent bonding. It is thought that this imparts an improved adherence of the base-coated substrate to the top coating via enhanced intermolecular hydrogen bonding and/or covalent bonding arising from the thermal curing of the base coating, the top coating, or both.

The top coating may be applied after the base coating is cured and comprises a biocompatible, polar polymer; that is, the top or second coating is applied on top of the cured base coating. The top coating, upon curing or drying, forms the integrated (both with itself and the base coating), flexible, and fluid-impermissible elongate wall of the housing having an interior and an exterior surface that will interact directly with the rotating impeller blades and the vasculature of a patient. This integrated coating for forming fluid-impermissible impeller housing 112 is desirably structurally stable, resists delamination, and strongly adheres to the metallic elongate structure 159 of housing mesh 202 (e.g., the nitinol or other shape memory alloy substrate), such that delamination of the polymeric material from the base coated metallic mesh (housing) is minimized or eliminated altogether. Polymers suitable for use in the top coating can be selected from the group consisting of a functionalized flexible polyethylene resin such as a maleic anhydride-grafted linear low density polyethylene, a thermoplastic elastomer material selected from commercially-available Hytrel® poly (ether-ester) copolymer resin family, a thermoplastic elastomer material selected from commercially-available Pebax® or Elastamid® E poly(ether-block-amide) copolymer resin family, a thermoplastic polyurethane resin based on different hard-segment and/or soft-segment types such as the one selected from commercially available Elasthane™ or Pellethane® poly(ether-urethane) resin family, or Pursil® or Elast-Eon® silicone-poly(ether-urethane) resin family, Bionate® poly(carbonate-urethane) resin family, Carbosil® silicone-poly(carbonate-urethane) resin family, and a Thoralon® thermoplastic silicone-poly(urethane urea) material made of an aromatic diisocyanate, a polyether glycol, a dihydroxylated silicone, a diol and a diamine chain extender, and combinations thereof. Desirably, in one specific embodiment, the biocompatible polymer used for the top coating is selected from the group comprising commercially-available thermoplastic polyurethane resins or thermoplastic polyurethane/urea resins based on different hard-segment and/or soft-segment types, such as poly(ether-urethane) resin family (Elasthane™, Pellethane®, and the like), or silicone-poly (ether-urethane) resin family (Pursil®, Elast-Eon®, and the like), or poly(carbonate-urethane) resin family (Bionate® and the like), or silicone-poly(carbonate-urethane) resin family (Carbosil® and the like), or desirably, a Thoralon® silicone-poly(ether urethane/urea) resin.

In yet another aspect, the top coating is selected from the group consisting of a biocompatible thermoplastic polyurethane/polyurea resin or blend, a biocompatible block polymer resin or blend, a thermoplastic poly(ether urethane), thermoplastic poly(carbonate urethane), thermoplastic silicone-poly(ether urethane), thermoplastic silicone-poly(carbonate urethane), silicone-poly(ether urethane/urea) and combinations thereof. Desirably, the polymer is a Thoralon® polymer.

In yet another aspect, a desirable thermoplastic polyurethane, polyurea, and/or poly(urethane urea) material used for the top coating is a biocompatible, segmented block copolymer comprising a hard urethane or urea segment type derived from an aromatic or aliphatic diisocyanate and a diol and/or diamine chain extender and the flexible segment type derived from one or more polyol(s) such as polyester glycol(s), polyether glycol(s), polycarbonate glycol(s), dihydroxylated silicone polymer(s) and any combination thereof. One or more thermoplastic polyurethane, polyurea or poly (urethane urea) resin material(s) having different hard-segment type(s) and different soft-segment type(s) can be concurrently used as a polymer blend to adjust the mechanical flexibility of the cured top coating material and thus to achieve the desired collapsibility and self-expandability for coated impeller housing 116. In some aspects, the segmented thermoplastic polyurethane and/or polyurea and poly(urethane/urea) block copolymer(s) will have a constituent urethane and/or urea functional group that exhibits enhanced intermolecular hydrogen bonding with the $R^1$ functional group of the multifunctional organosilane coupling compound(s) and/or rich amine/amino or hydroxyl species on the base coating surfaces. These functional groups may also provide active sites for covalent bonding possibly arising from the thermal curing of the top coating, as illustrated in FIGS. 6A, 6B and 6C.

In a desirable embodiment, a biocompatible polymer resin material is selected, a top coating solution is prepared using a polar, volatile solvent selected from the group including THF (tetrahydrofuran), DMAc (dimethylacetamide), NMP (N-methyl-2-pyrrolidone), dimethyl sulfoxide, and the like at a concentration of 0.5 to 25% (v/v) or 5 to 20% (v/v).

As illustrated in FIGS. 6A, 6B and 6C, the reactant in the top coating may comprise an amino (amine), an isocyanate, an epoxy (oxirane) or a combination thereof, as disclosed elsewhere herein based on the organofunctional group $R^1$ of the organosilane coupling compound used for the base coating. This may provide some enhanced adherence of the top coating with the base coating in that some covalent bonding may arise from the curing of the top coating conducted at a temperature of from 30 to 100° C., or from 60 to 90° C., for some time ranging from 1 to 24 hours.

In yet another aspect, the top coating comprises a thermally-curable liquid polymer system, including, but not limited to, commercially-available products like Steralloy® series two-part liquid polyurethane compounds or other similar thermally-curable liquid urethane/urea systems.

In some embodiments, the top coating polymer is a thermoplastic polyurethane-urea. Formation of a polyurethane-urea as the top coating comprises the reaction of a polyurethane or polyurea prepolymer having diisocyanate terminal groups with a diol and/or diamine as a chain extender. Attachment of a top coating to the base coating is done using the reaction of the prepolymer with chain extender(s) as described elsewhere herein.

In some embodiments, the top coating polymer comprises a curable liquid urethane or urea or urethane-urea system that generally include (i) a prepolymer and at least one chain extender as a two-part, liquid reactive system, or (ii) an isocyanate or a diisocyanate, a polyhydroxyl compound and at least one chain extender as a one-part liquid reactive system. The top coating polymer may further comprise a crosslinker, a catalyst or both. After the completion of curing, the top coating comprises a thermoplastic, or thermosetting, polyurethane or polyurea or polyurethane/urea material layer. The prepolymer used in such a two-part liquid reactive system comprises the reaction product of an excessive diisocyanate with one or more polyhydroxyl compound.

The diisocyanate is a compound of Formula (III),

(III)

wherein $R^4$ is selected from the group consisting of substituted or unsubstituted aryl, heteroaryl, alkyl, alkenyl, and alkynyl; or $R^4$ is Ar-L-Ar where Ar is an aryl or heteroaryl ring system, and L is defined as an alkyl chain or linkage.

In some embodiments, $R^4$ is Ar-L-Ar where L is a $(CH_2)_n$, and n is from 1 to 5. In yet another embodiment, Ar is phenyl with no additional substituents, and n=1.

In yet another aspect, $R^4$ is selected from the group consisting of substituted or unsubstituted aryl, heteroaryl, alkyl, alkenyl, and alkynyl; or $R^4$ is Ar-L-Ar where Ar is an aryl or heteroaryl ring system, or $R^4$ is Rr-L-Rr where Rr is an alkyl or heteroalkyl ring system, and L is a spacing group independently selected from the group consisting of a bond and $(CH_2)_n$ where n is a number from 1 to 10.

Aryl or heteroaryl groups may be optionally substituted or unsubstituted, in addition to the diisocyanate substitutions. Additional substituents are selected from the group consisting of halides, alkyl, hydroxy, cyano, nitro, and alkoxy. Substituents can be on any location of the aromatic ring not taken by either the isocyanate or the spacing group L. Examples of aryl groups include, but are not limited to, phenyl, naphthyl, anthracyl, phenanthracyl, fluorenyl and indenyl.

Heteroaryl rings may have from five to 12 atoms in the ring and comprise one or more heteroatoms selected from N, S, and O. Examples of heteroaryl rings include, but are not limited to, furyl, thienyl, oxazolyl, isoxazolyl, thiazolyl, isothiazolyl, 1,2,3-oxadiazolyl, 1,2,4-oxadiazolyl, 1,3,4-oxadiazolyl, 1,2,5-oxadiazolyl, 1,2,3-thiadiazolyl, 1,2,4-thiadiazolyl, 1,3,4-thiadiazolyl, 1,2,5-thiadiazolyl, pyrimidinyl 1,2,3-triazinyl, benzofuryl, benzisofuryl, benzothienyl, benzisothienyl, indolyl, isoindolyl, indazolyl, benzothiazolyl, benzisothiazolyl, benzoxazolyl, benzisoxazolyl, benzirnidazolyl, quinolinyl, isoquinolinyl, cinnolinyl, phthalazinyl, quinazolinyl, quinoxalinyl, naphthyridinyl, benzotriazinyl, purinyl, pteridinyl and indolizinyl.

As used herein, the term "alkyl" is defined as a straight or branched chain, or cyclic hydrocarbon, or combination thereof, which may be fully saturated, mono- or polyunsaturated and can include di- and multivalent radicals, having from 1 to 20 carbon atoms. Examples of saturated hydrocarbon radicals include, but are not limited to, methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers.

As used herein, the term "heteroalkyl" is defined as a stable straight or branched chain, or cyclic hydrocarbon, or combinations thereof, consisting of from 1 to 20 carbon atoms and from one to three heteroatoms selected from the group consisting of O, N, S, and wherein the nitrogen and sulfur atoms may optionally be oxidized and the nitrogen heteroatom may be quaternary. The heteroatom(s) O, N and S may be placed at any interior position of the heteroalkyl group. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$.

Examples of heteroalkyl rings, alternatively referred to as heterocycles, include, but are not limited to, 1H-indazole, 2-pyrrolidonyl, 2H,6H-1,5,2-dithiazinyl, 2H-pyrrolyl, 3H-indolyl, 4-piperidonyl, 4aH-carbazole, 4H-quinolizinyl, 6H-1,2,5-thiadiazinyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazalonyl, carbazolyl, 4aH-carbazolyl, β-carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxazolidinylperimidinyl, phenanthridinyl, phenanthrolinyl, phenarsazinyl, phenazinyl, phenothiazinyl, phenoxathiinyl, phenoxazinyl, phthalazinyl, piperazinyl, piperidinyl, pteridinyl, piperidonyl, 4-piperidonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, pyrrolyl, quinazolinyl, quinolinyl, 4H-quinolizinyl, quinoxalinyl, quinuclidinyl, carbolinyl, tetrahydrofuranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, tetrazolyl, and xanthenyl. In some embodiments, the heterocycles include, but are not limited to, pyridinyl, thiophenyl, furanyl, indazolyl, benzothiazolyl, benzimidazolyl, benzothiaphenyl, benzofuranyl, benzoxazolyl, benzisoxazolyl, quinolinyl, isoquinolinyl, imidazolyl, indolyl, isoidolyl, piperidinyl, piperidonyl, 4-piperidonyl, piperonyl, pyrrazolyl, 1,2,4-triazolyl, 1,2,3-triazolyl, tetrazolyl, thiazolyl, oxazolyl, pyrazinyl, and pyrimidinyl, and fused ring and spiro compounds containing the above heterocycles.

Examples of alkyl rings, alternatively referred to as carbocycles or cycloalkyl groups, include any stable 3, 4, 5, 6, or 7-membered monocyclic or bicyclic or 7, 8, 9, 10, 11, 12, or 13-membered bicyclic or tricyclic, any of which may be saturated or partially unsaturated. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane (decalin), [2.2.2]bicyclooctane, indanyl, adamantyl, and tetrahydronaphthyl (tetralin).

The polyhydroxyl compound is predominantly linear and has a weight average molecular weight of from about 200 to about 10,000, or from about 500 to about 4000. The most suitable polyhydroxyl compound includes the group selected from polyalkylene ether glycols, dihydroxyl polyesters, dihydroxyl polycarbonates, dihydroxyl silicones, dihydroxyl polyesteramides, and etc.

The chain extenders may be selected from the group consisting of diols, diamines, aminoalcohols and combinations thereof. The two functional groups (hydroxyl or amino/amine) are separated by from one to 20 methylene units. The methylene chain may be branched or unbranched. In some aspects, the two functional groups are separated by from one to 20 ethylene glycol groups in the form of a poly(ethylene glycol) or poly(ether). One or more different chain extenders can be combined for application of the top coating.

Examples of chain extenders that are diols include, but are not limited to, ethylene glycol, propylene glycol, 1,4-butanediol, 1,5-pentanediol, 1,6-hexanediol, 1,7-hepatnediol, 1,8-octanediol, 1,9-nonanediol, 1,10-decanediol, and 1,4-cyclohexanediol. Examples of chain extenders that are diamines include, but are not limited to, ethylenediamine, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, and 1,4-diaminocyclohexane. Examples of chain extenders that are aminoalcohols include, but are not limited to, ethanolamine, 3-aminopropan-1-ol, 4-aminobutan-1-ol, 5-aminopentan-1-ol, 6-aminohexan-1-ol, 7-aminoheptan-1-ol, 8-aminooctan-1-ol, 9-aminononan-1-ol, 10-aminodecan-1-ol.

The top coating desirably exhibits a mechanical strength sufficient to withstand use as the impeller housing of a heart pump where the impeller is rotating at extremely high speeds. At the same time the top coating is sufficiently flexible to withstand compression and deformation of the housing mesh during insertion and removal of the heart pump. As such, in some embodiments the hardness of the top coating ranges from 60 A to 90 A, and up to 40 D as measured on the Shore Hardness Scale. In some aspects, the Shore Hardness of the top coating is about 60 A, about 70 A, about 80 A, about 90 A, about 100 A, about 10 D, about 20 D, about 30 D, about 40 D or about 50 D. As used herein, "about" means within ±5 hardness units on the reference scale (i.e., the Shore A or Shore D scale).

Also disclosed herein are various methods for coating a substrate that comprises a shape memory alloy, such as nitinol. In one embodiment, the method comprises applying a cleaning solution to the substrate thereby making a cleaned substrate; applying a first coating solution to the cleaned substrate; optionally rinsing the substrate with a solvent thereby making a rinsed substrate; curing the rinsed substrate thereby making a base coated substrate; applying a second coating solution to the base coated substrate; and curing the substrate thereby making the coated substrate.

Figure 8:
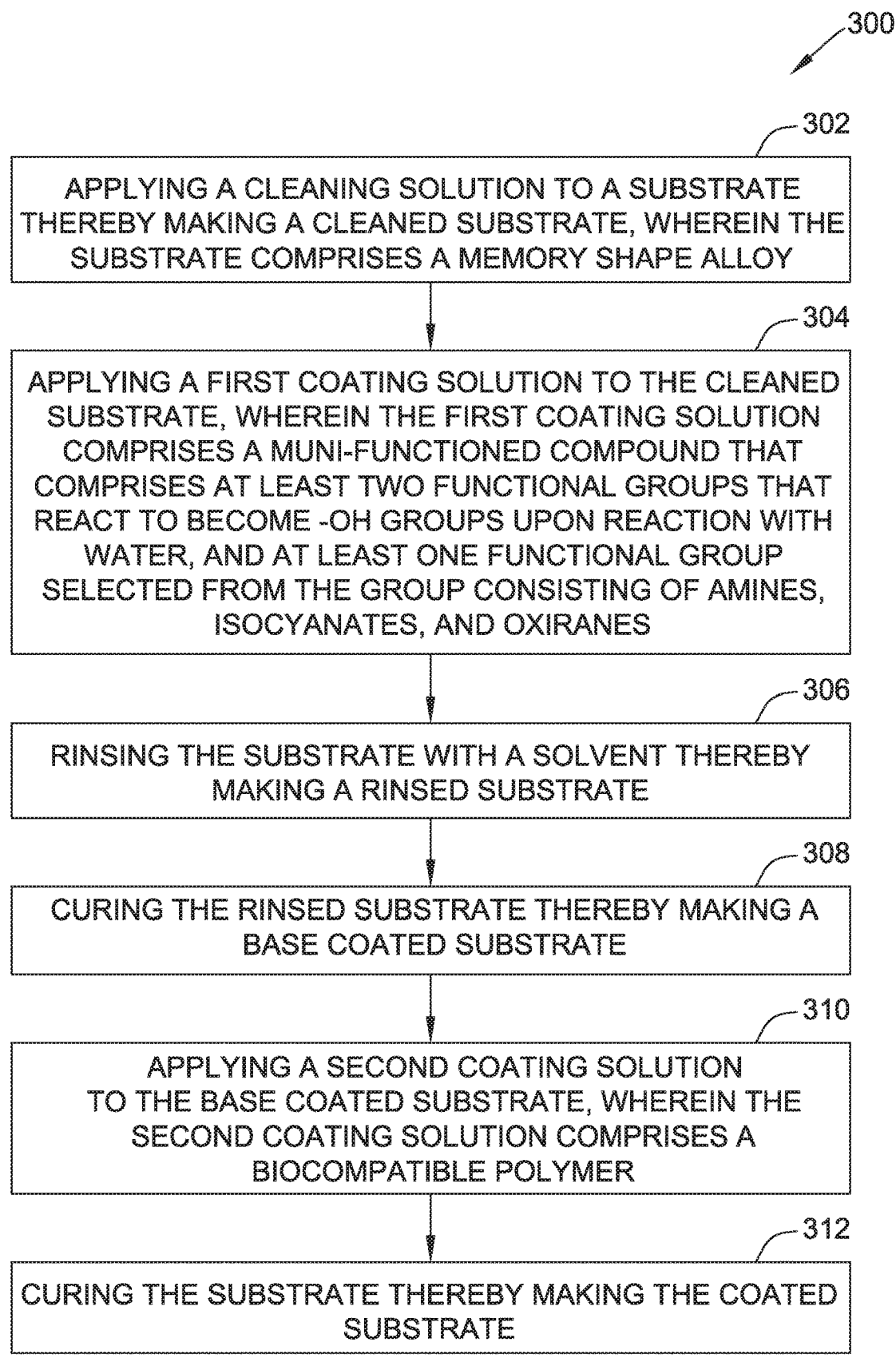
FIG. 8 is a flow diagram illustrating one embodiment of a method of forming a polymer coating on a substrate comprising a shape memory alloy.

FIG. 8 illustrates a flow diagram for one embodiment of method 300 for applying a coating to a substrate that comprises a shape memory alloy. Method 300 comprises: applying 302 a cleaning solution to the substrate that comprises a shape memory alloy followed by applying 304 a first coating solution to the cleaned substrate. Method 300 additionally includes rinsing 306 the substrate and curing 308 the rinsed substrate to make the base coated substrate. Finally, method 300 includes applying 310 a second coating solution to the based coated substrate and curing 312 the substrate to make the coated substrate. It is recognized that additional steps in this method may be necessary or that modifications of these steps may done and still remain within the scope of the disclosure.

In some embodiments of the present disclosure, the substrate that comprises a shape memory alloy is an impeller housing for a heart pump. In another aspect, the top coating and base coating as disclosed elsewhere herein are applied using this method. Any embodiment disclosed herein can be applied or combined with any other embodiment also disclosed herein.

The cleaning solution is selected to remove any debris on the surface of the substrate and/or remove any impurities that would affect adherence of the coating to the substrate. In some aspects, the cleaning solution is an alcohol. In yet another aspect, the cleaning solution comprises a Lewis acid or a Lewis base. One example of a cleaning solution suitable for use herein is a corrosive Lewis acid solution of iron(II) chloride ($FeCl_2$). Other Lewis acids as are known in the art are also encompassed herein. Alcohols suitable for cleaning the substrate are methanol, ethanol and isopropanol. Other alcohols as are known in the art also encompassed herein. In some embodiments, the substrate may also be cleaned and rinsed with the solvent, which will be used to form the base coating. In some aspects, the substrate is cleaned with more than one cleaning solution.

After cleaning, a base coating as described elsewhere herein is applied to the substrate. Application to the substrate may be done using methods known in the art; examples include, but are not limited to, dip-coating, spraying, and submersing. Desirably, the multifunctional organosilane compound or compounds in the base coating are applied to the substrate by dip-coating. After applying the base coating, the substrate is cured. Curing may be done at ambient temperature or at elevated temperature. In some aspects, the curing temperature is approximately 50° C., 75° C., 100° C., 125° C., 150° C., or 175° C. In yet another aspect, the curing temperature is between 50° C. and 200° C. In yet another aspect, the curing temperature will be selected such that the curing is complete and the solvent has evaporated in less than 60 minutes, less than 30 minutes, or less than 15 minutes.

Additionally, curing may be done at atmospheric pressure or under reduced pressure. In some aspects, the reduced pressure is below 0.8 atm, below 0.6 atm, below 0.4 atm, below 0.2 atm, below 0.15 atm, below 0.10 atm, below 0.05 atm, or below 0.01 atm.

Rinsing the substrate after applying the base coating and before curing is optionally done if excessive liquid film is present on the substrate. Rinsing is with a solvent that will not wash away the multifunctional organosilane compound present on the surface of the substrate. Examples of the rinse solvent include, but are not limited to, methanol, ethanol, isopropanol, water, and combinations thereof.

Applying the top coating to the substrate that comprises the base coating is done using methods known in the art; examples include, but are not limited to, dip-coating, spraying and submersing. Desirably, the top coating is applied by dip-coating. Dip-coating can be done multiple times to create a top coating of sufficient thickness. In some aspects the dip-coating is done one time, two times, three times, four times, or five times. After each application, the substrate may optionally be cured using the same or different curing conditions as described herein. In some aspects, the substrate may not be cured between dips in the top coating solution. The solution used for applying the top coating comprises a biocompatible polymer material with one or more solvents or a reactive polymer system that comprises an isocyanate prepolymer, chain extender(s)/crosslinker(s), and optionally catalyst(s) with one or more solvents, as described elsewhere herein. Desirably, the biocompatible polymer for a top coating comprises any thermoplastic polyurethane resin or any thermoplastic polyurea resin, or any thermoplastic poly(urethane-urea) copolymer resin or combinations thereof. In some embodiments, the reactive polymer system for a top coating comprises a two-part polyurethane, polyurea, or poly(urethane-urea) system having an isocyanate prepolymer as one part and chain extender (s)/crosslinker(s) and, in some embodiments, a catalyst as the other part. In some embodiments, the biocompatible, polar polymer, or the reactive polymer system, used for a top coating solution may be commercially available and used herein.

Curing the substrate after the application of the top coating can be done in a similar manner as to curing after the application of the base coating. After applying the top coating, the substrate is cured. Curing may be done at ambient temperature or at elevated temperature. In some aspects, the curing temperature is approximately 30° C., 40° C., 50° C., 75° C., or 105° C. In yet another aspect, the curing temperature is between 50° C. and 100° C. In yet another aspect, the curing temperature will be selected such that the curing is complete and the solvent has evaporated in less than 60 minutes, less than 30 minutes, or less than 15 minutes. Additionally, curing may be done at atmospheric pressure or under reduce pressure. In some aspects, the reduced pressure is below 0.8 atm, below 0.6 atm, below 0.4 atm, below 0.2 atm, below 0.15 atm, below 0.10 atm, below 0.05 atm, or below 0.01 atm.

EXAMPLES

The present disclosure is further illustrated by the following Examples, which are provided as illustrative only and are not meant to be limiting in any manner.

The general procedure for preparing the different embodiments in the following Examples is as follows: a first or base coating solution containing multifunctional organosilane compound(s) was prepared in a proper solvent. A test substrate comprising nitinol was used to test the adherence of different coating compositions. The test substrate was cleaned, dried and dipped into the base coating solution followed by drying and curing. A second or top coating solution comprising a selected polymer system was prepared, and the test substrate coated with the cured base coating was dipped at least once into this solution. The top-coated substrate was dried and cured. Adherence of the top polymer coating on the base-coated substrate was tested in accordance with ASTM C794-15A as described below (sometimes called "the adhesion-in-peel test").

Preparation of Top-Coating Solution with Thoralon® Polyurethane/Urea

Methylene diphenyl diisocyanate was reacted with a poly(tetramethylene oxide) glycol in N,N-dimethylacetamide (DMAc) solvent to form an isocyanate prepolymer (part A). To the prepolymer solution in DMAc (part A) was added part B comprising 1,4-butanediol and ethylene diamine chain extenders. With continuous mixing or stirring, the mixture of part A and B react at 70° C. for six hours. The resultant Thoralon® polyeurethane/urea solution was diluted to different concentrations having different solid content by adding DMAc solvent, and used as the top coating solutions for dip coating the substrate with no base coating or each of different base coatings as described below. In some examples, an additional reactant was added to a base or top coating solution before applying the solution.

Preparation of Control (No Base Coating)

Natural nitinol bars having a dimension of 3.5" long by 1" wide by 0.006" thick (the test substrate) were cleaned with isopropyl alcohol (IPA), washed with a ferrous chloride ($FeCl_2$) corrosive solution, and dried at 80° C. for one hour. The bars were directly coated with multiple passes using a 10% Thoralon® polyurethane/urea solution in DMAc solvent and the coating mold shown in FIG. 7, and then cured/dried at 60° C. for 1 hour or until DMAc solvent evaporated. After 48 hours ambient conditioning, the adhesion-in-peel tests on the coated nitinol bars were conducted (shown in FIG. 7). The maximum peel forces are indicative of the adherence strength of polyurethane coating films on the nitinol surfaces.

Example 1

The base coating solution was prepared by adding 2% (3-glycidyloxypropyl)trimethoxysilane to a solution of 95% ethanol and 5% water. The solution, whose pH value was adjusted to 4.5 to 5.5 by adding acetic acid, was allowed to hydrolyze and chemically stabilize for 20 min. The cleaned nitinol bars were dip-coated, briefly rinsed by immersion into a 95% aqueous ethanol solvent, and cured at 110° C. for 10 min in a vacuum oven. The base-coated bars were then top-coated, cured/dried, conditioned, and tensile-tested in the same way as the Control Coating.

Example 2

The base coating solution was prepared by addition of 2% bis(3-(trimethoxysilyl)propyl)amine to a solution of 95% ethanol and 5% water. The solution was allowed to hydrolyze and chemically stabilize for 20 min. The cleaned nitinol bars were dip-coated, briefly rinsed by immersion into a 95% aqueous ethanol solvent, and cured at 110° C. for 10 min in a vacuum oven. The base-coated bars were then top-coated, cured/dried, conditioned, and tensile-tested in the same way as in the Control Coating.

Example 3

The base coating solution was prepared by addition of 2% (3-aminopropyl)trimethoxysilane to a solution of 95% ethanol and 5% water. The solution was allowed to hydrolyze and chemically stabilize for 20 min. The cleaned nitinol bars were dip-coated, briefly rinsed by immersion into a 95% aqueous ethanol solvent, and cured at 110° C. for 10 min in a vacuum oven. The base-coated bars were then top-coated, cured/dried, conditioned, and tensile-tested in the same way as in the Control Coating.

Example 4

The base coating solution was prepared by addition of a 2% blend of (3-glycidyloxypropyl)trimethoxysilane (GOPT-MOS) and bis(3-(trimethoxysilyl)propyl)amine (BT-MOSPA) (1:5 w/w ratio) in a solution of 95% ethanol and 5% water. The solution was allowed to hydrolyze and chemically stabilize. When the container was open to air, no gelation or change in optical turbidity was observed for at least two days after preparation, indicative of a long shelf life.

The cleaned nitinol bars were dip-coated, briefly rinsed by immersion into a 95% aqueous ethanol solvent, and cured at 110° C. for 10 min in a vacuum oven. The base-coated bars were then top-coated, cured/dried, conditioned, and tensile-tested in the same way as in the Control Coating.

Example 5

The base coating solution was prepared by addition of a 2% blend of (3-aminopropyl)trimethoxysilane (APTMOS) and bis(3-(trimethoxysilyl)propyl)amine (BTMOSPA) (1:5 w/w ratio) into a solution of 95% ethanol and 5% water. The solution was allowed to hydrolyze and chemically stabilize. When the container was open to air, no gelation or change in optical turbidity was observed for at least two days after preparation, indicative of a long shelf life.

The cleaned nitinol bars were dip-coated, briefly rinsed by immersion into a 95% aqueous ethanol solvent, and cured at 110° C. for 10 min in a vacuum oven. The base-coated bars were then top-coated, cured/dried, conditioned, and tensile-tested in the same way as in the Control Coating.

Example 6

The base coating solution was prepared by addition of a 2% blend of (3-glycidyloxypropyl)trimethoxysilane (GOPT-MOS) and Jeffamine® D-230 (1:2 w/w ratio), which is a polyetheramine (PEA) or an amine reactant, into a solution of 95% ethanol and 5% water. The solution was allowed to hydrolyze and chemically stabilize for 20 min. The cleaned nitinol bars were dip-coated, briefly rinsed by immersion into a 95% aqueous ethanol solvent, and cured at 110° C. for 10 min in a vacuum oven. The base-coated bars were then top-coated, cured/dried, conditioned, and tensile-tested in the same way as in the Control Coating.

Example 7

The base coating solution was prepared by addition of 2% blend of (3-glycidyloxypropyl)trimethoxysilane (GOPT-MOS), Jeffamine® D-230 and bis(3-(trimethoxysilyl)pro-pyl)amine (BTMOSPA) (1:2:8 w/w/w ratio) into a solution of 95% ethanol and 5% water. The solution was allowed to hydrolyze and chemically stabilize for 20 min. When the container was open to air, no gelation or change in optical turbidity was observed for at least two days after prepara-tion, indicative of a long shelf life.

The cleaned nitinol bars were dip-coated, briefly rinsed by immersion into a 95% aqueous ethanol solvent, and cured at 110° C. for 10 min in a vacuum oven. The base-coated bars were then top-coated, cured/dried, conditioned, and tensile-tested in the same way as in the Control Coating.

Example 8

The base coating solution was prepared by addition of a 2% blend of (3-glycidyloxypropyl)trimethoxysilane (GOPT-MOS) and bis(3-(trimethoxysilyl)propyl)amine (BT-MOSPA) (1:5 w/w ratio) into a solution of 95% ethanol and 5% water. The solution was allowed to hydrolyze and chemically stabilize for 20 min. When the container was open to air, no gelation or change in optical turbidity was observed for at least two days after preparation, indicative of a long shelf life.

The cleaned nitinol bars were dip-coated, briefly rinsed by immersion into a 95% aqueous ethanol solvent, and cured at 110° C. for 10 min in a vacuum oven. The base-coated bars were then top-coated, cured/dried, conditioned, and tensile-tested in the same way as in the Control Coating, except that the top coating system comprised 10% Thoralon® polyure-thane material with addition of Jeffamine® D-230 (1:20 v/v ratio).

Example 9

The base coating solution was prepared by addition of a 2% blend of (3-aminopropyl)-trimethoxysilane (APTMOS) and bis(3-(trimethoxysilyl)propyl)amine (BTMOSPA) (1:5 w/w ratio) to a solution of 95% ethanol and 5% water. The solution was allowed to hydrolyze and chemically stabilize for 10 min. When the container was open to air, no gelation or change in optical turbidity was observed for at least two days after preparation, indicative of a long shelf life.

The cleaned nitinol bars were dip-coated, briefly rinsed by immersion into a 95% aqueous ethanol solvent, and cured at 110° C. for 10 min in a vacuum oven. The base-coated bars were then top-coated, cured/dried, conditioned, and tensile-tested in the same way as in the Control Coating.

Example 10

The base coating solution was prepared by addition of a 3% blend of (3-isocyanatopropyl)trimethoxysilane (IPT-MOS) and Jeffamine® D-230 (1:1 w/w ratio) to a solution of 95% ethanol and 5% water. The solution was allowed to hydrolyze and chemically stabilize for 20 min. The cleaned nitinol bars were dip-coated, briefly rinsed by immersion into a 95% aqueous ethanol solvent, and cured at 110° C. for 10 min in a vacuum oven. The base-coated bars were then top-coated, cured/dried, conditioned, and tensile-tested in the same way as in the Control Coating.

Example 11

The base coating solution was prepared by addition of a 3% blend of (3-isocyanatopropyl)-trimethoxysilane (IPT-MOS) and bis[(3-methyldimethoxysilyl)-propyl]-polypro-pylene oxide (BMDMOSPPO) (1:1 w/w ratio) to a solution of 95% ethanol and 5% water. The solution, whose pH value was adjusted to 4.5 to 5.5 using acetic acid, was allowed to hydrolyze and chemically stabilize for 20 min. When the container was open to air, no gelation or change in optical turbidity was observed for at least two days after prepara-tion, indicative of a long shelf life.

The cleaned nitinol bars were dip-coated, briefly rinsed by immersion into a 95% aqueous ethanol solvent, and cured at 110° C. for 10 min in a vacuum oven. The base-coated bars were then top-coated, cured/dried, conditioned, and tensile-tested in the same way as in the Control Coating, except that the top coating solution comprised 10% Thoralon® poly-urethane solution in DMAc with addition of small amount of Jeffamine® D-230 (30:1 v/v ratio).

Coating Adhesion Testing ("the Adhesion-in-Peel Test")

The strength of the adhesion of the polymer coating was tested according to ASTM C794-15A—"Standard Test Method for Adhesion-in-Peel of Elastomeric Joint Sealants."

Figure 7:
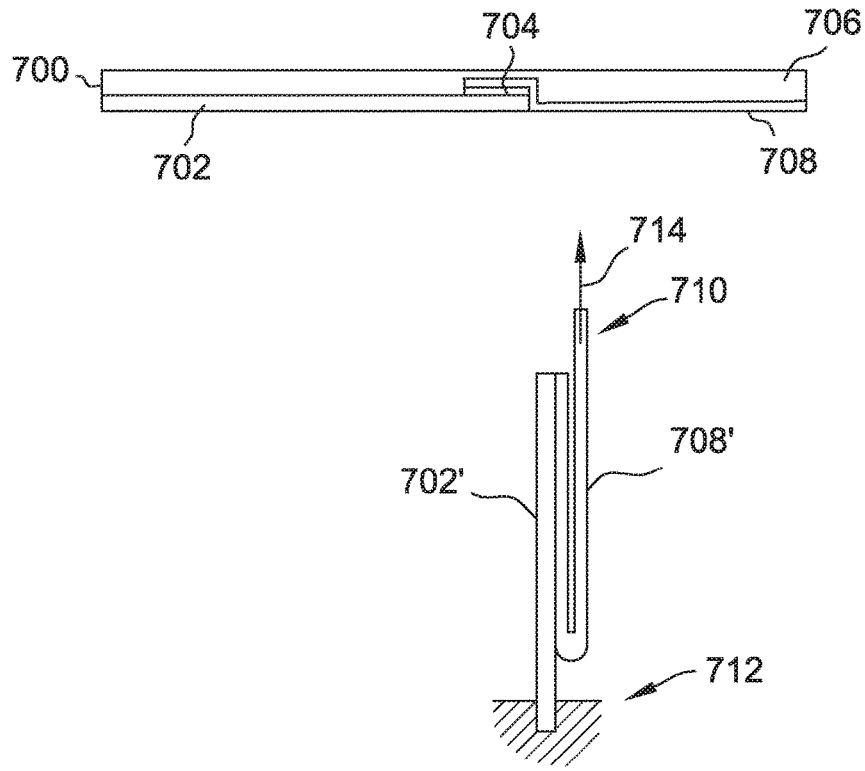
FIG. 7 illustrates a mold for applying a base coating and a top coating on a nitinol substrate and an adhesion-in-peel test for determining the layer to layer adherence between a base coating and a top coating on the substrate, respectively.

A nitinol substrate strip, 0.006" thick by 1" wide by 3.5" long, was cut from a nitinol sheet, and cleaned using 70% isopropyl alcohol. The strip was coated using a base coating and cured at 110° C. for about 10 min. As shown in FIG. 7, the base coated nitinol strip 702 was masked with a thin PTFE tape 704 by 0.5" in length at one end, and then placed into the rectangular cavity 706 of a coating mold 700 (ca. 6.5" long by 1" wide by 0.016" deep) with its masked end located in the middle of the mold cavity and its free end aligned with an end of the mold cavity 706. A flexible piece of lint-free, polyester fabric cloth 708 (1" wide by 3.5" long) was then aligned with the mold cavity, and placed atop the base-coated nitinol strip to have about 0.5" overlapping length with the PTFE-masked end of the base-coated nitinol strip 702. After the strip and fabric were properly placed into a coating mold, a top coating was applied to the mold cavity 706 wherein the base-coated strip and the cloth were top-coated, except the PTFE-masked end of the base-coated nitinol strip. The top-coated strip and cloth in the mold were placed into a vacuum oven, and cured/dried at 60° C. for a minimum of 18 hours. The top-coated sample was conditioned under ambient condition for at least 48 hours prior to the adhesion-in-peel test (also shown in FIG. 7) by using a MTS tensile tester, where the PTFE-masked strip end of the top-coated substrate 702' was affixed to the lower fixture 712 while the free end of the top-coated cloth 708' was affixed to the upper fixture 710. During the adhesion-in-peel test, the upper fixture 710 moves upwards at a constant crosshead speed of 2"/min, under which the top coating was gradually peeled from the bare or base-coated nitinol strip 702. The adhesion strength of the top coating onto the nitinol was comparatively quantified by the maximum peel force 714 measured during the test.

Results

As shown in Table 1, the addition of a base coating greatly increases the adherence of a top coating comprised of a thermoplastic poly(urethane-urea) or a thermoplastic polyurethane polymer to the surface of a nitinol substrate based on the results of the adhesion-in-peel test. A base coating composition comprising one or more organosilane coupling compounds increased the adhesion strength; however, the binary and trinary mixtures of different organosilanes having different functional groups selected from amine/amino, or isocyanate or oxirane groups or the mixture of a single organosilane compound with the addition of an amine reactant like polyetheramine produced the greatest increase in adhesion strength. Similarly, the addition of an amine reactant, like a polyetheramine, to the top coating enhanced the adhesion to the nitinol substrate coated by a base coating having one or more organosilane coupling compound(s).

TABLE 1

| Example | Base Coat | Top Coat | Adhesion Strength (lbf) |
|---|---|---|---|
| Control | None | Thoralon ® | 0.5 |
| 1 | (3-glycidyloxypropyl)-trimethoxysilane (GOPTMOS) | Thoralon ® | 2.2 |
| 2 | bis(3-(trimethoxysilyl)-propyl)amine (BTMOSPA) | Thoralon ® | 6.2 |
| 3 | (3-aminopropyl)-trimethoxysilane (APTMOS) | Thoralon ® | 10.2 |
| 4 | GOPTMOS:BTMOSPA | Thoralon ® | 14.2 |
| 5 | APTMOS:BTMOSPA | Thoralon ® | 16.2 |
| 6 | GOPTMOS:polyetheramine (PEA) | Thoralon ® | 15.2 |
| 7 | GOPTMOS:PEA:BTMOSPA | Thoralon ® | 15.6 |
| 8 | GOPTMOS:BTMOSPA | Thoralon ®:PEA | 15.0 |
| 9 | APTMOS:BTMOSPA | Thoralon ® | 16.2 |
| 10 | IPTMOS:PEA | Thoralon ® | 15.3 |
| 11 | IPTMOS:BMDMOSPPO | Thoralon ®:PEA | 15.3 |

Although the embodiments and examples disclosed herein have been described with reference to particular embodiments, it is to be understood that these embodiments and examples are merely illustrative of the principles and applications of the present disclosure. It is therefore to be understood that numerous modifications can be made to the illustrative embodiments and examples and that other arrangements can be devised without departing from the spirit and scope of the present disclosure as defined by the claims. Thus, it is intended that the present application cover the modifications and variations of these embodiments and their equivalents.

This written description uses examples to disclose the disclosure, including the best mode, and also to enable any person skilled in the art to practice the disclosure, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. An impeller assembly for a heart pump, the impeller assembly comprising:
    an impeller shaft;
    an impeller blade extending from the impeller shaft;
    an impeller housing in which the impeller shaft is journaled for rotation, wherein the impeller housing comprises a metallic mesh and includes an impeller blade zone, an inlet zone, an outlet zone, and an elongate wall structure; and
    a polymer coating on the metallic mesh, the polymer coating comprising a base coating in direct contact with the metallic mesh and a top coating in direct contact with the base coating, wherein the top coating is integral with the base coating and itself to thereby render the elongate wall structure fluid-impermissible.

2. The impeller assembly according to claim 1, wherein the base coating is chemically bonded to the metallic mesh and the top coating is adhered to and integral with the base coating via intermolecular hydrogen bonding, covalent bonding, or both, to thereby provide the fluid-impermissible elongate wall structure having smooth interior and exterior surfaces.

3. The impeller assembly according to claim 1, wherein the base coating comprises at least one multifunctional organosilane compound that comprises at least two functional groups that chemically convert to silanol functional groups upon reaction with water, and at least one functional group selected from the group consisting of amines, isocyanates, and oxiranes, and wherein the multifunctional organosilane compound is suitable for application to the metallic mesh as a thin film layer less than 100 μin thick.

4. The impeller assembly according to claim 3, wherein the multifunctional organosilane compound is a compound of Formula (I) or (II),

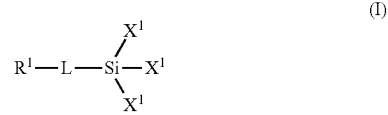

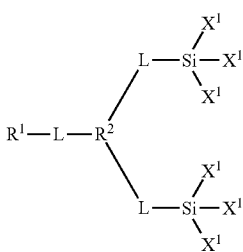

(II)

wherein each $X^1$ is independently selected from the group consisting of hydrogen, hydroxy (—OH), alkoxy (OR$^3$), acyloxy (OCOR$^3$), oxime (—O—N=C(R$^3$)$_2$, amine (—N(R$^3$)$_2$), oxirane and halide;

$R^1$ is selected from the group consisting of hydrogen, —N(R$^3$)$^2$, isocyanate and oxirane;

each L is a spacing group independently selected from the group consisting of a bond and (CH$_2$)$_n$;

n is a number of from 1 to 20;

$R^2$ is selected from the group consisting of a bond, an amine, and (CH$_2$)$_n$ where one of the H atoms on a methylene is replaced with a -L-R$^1$ group; and each $R^3$ is independently selected from the group consisting of hydrogen and an alkyl group, where the alkyl group is a C$_1$ to C$_{10}$ straight chain or branched hydrocarbon.

5. The impeller assembly according to claim 3, wherein the base coating comprises two or three different multifunctional organosilane coupling compounds.

6. The impeller assembly according to claim 3, wherein the multifunctional organosilane coupling compound is selected from the group consisting of 3-aminopropyltriethoxysilane, 3-aminopropyltrimethoxysilane, 4-aminobutyltriethoxysilane, 4-amino-3,3-dimethylbutyl-trimethoxysilane, N-(2-aminoethyl)-3-aminopropyltriethoxysilane, N-(2-aminoethyl)-3-aminopropyltrimethoxysilane, N-(6-aminohexyl) aminomethyltrimethoxysilane, N-(6-aminohexyl) aminomethyltriethoxysilane, N-(α-aminoethy)-3-aminopropylsilanetriol, (3-glycidoxypropyl)trimethoxysilane, (3-glycidoxypropyl)triethoxysilane, 5,6-epoxyhexyltriethoxysilane, (3-glycidoxypropyl)methyldimethoxysilane, (3-glycidoxypropyl)methyldiethoxysilane, (3-glycidoxypropyl)dimethylmethoxysilane, (3-glycidoxypropyl)dimethylethoxysilane, (3-glycidoxypropyl)trimethoxysilane, (3-glycidoxypropyl)triethoxysilane, 5,6-epoxyhexyltriethoxysilane, (3-glycidoxypropyl)methyldimethoxysilane, (3-glycidoxypropyl)methyldiethoxysilane, (3-glycidoxypropyl)dimethylmethoxysilane, and (3-glycidoxypropyl)dimethylethoxysane, and combinations thereof.

7. The impeller assembly according to claim 1, wherein the top coating is selected from the group consisting of a biocompatible thermoplastic polyurethane/polyurea resin or blend, a biocompatible block copolymer resin or blend, a thermoplastic poly(ether urethane), thermoplastic poly(carbonate urethane), thermoplastic silicone-poly(ether urethane), thermoplastic silicone-poly(carbonate urethane), silicone-poly(ether urethane/urea) and combinations thereof.

8. The impeller assembly according to claim 1, wherein the top coating is a polyaddition product of a thermally-curable urethane or urethane/urea system that comprises a urethane/urea prepolymer and at least one chain extender or an isocyanate, at least one polyhydroxyl compound, and at least one chain extender.

9. The impeller assembly according to claim 8, wherein the polyaddition product further comprises a crosslinker, a catalyst or both.

10. The impeller assembly according to claim 8, wherein the polyaddition product forms a prepolymer that is chemically derived from a reaction of an isocyanate and at least one polyhydroxyl compound.

11. The impeller assembly according to claim 10, wherein the prepolymer further comprises a catalyst.

12. The impeller assembly according to claim 10, wherein the isocyanate is a diisocyanate of Formula (III),

(III)

wherein $R^4$ is selected from the group consisting of substituted or unsubstituted aryl, heteroaryl, alkyl, alkenyl, and alkynyl; or $R^4$ is Ar-L-Ar where Ar is an aryl or heteroaryl ring system, or $R^4$ is Rr-L-Rr where Rr is an alkyl or heteroalkyl ring system, and L is a spacing group independently selected from the group consisting of a bond and (CH$_2$)$_n$ where n is a number from 1 to 10.

13. The impeller assembly according to claim 10, wherein the polyhydroxyl compound is selected from the group consisting of polyalkylene ether glycols, dihydroxyl polyesters, dihydroxyl polycarbonates, dihydroxyl silicones, dihydroxyl polyesteramides, and combinations thereof.

14. The impeller assembly according to claim 10, wherein the polyhydroxyl compound has molecular weight from 200 to 10,000.

15. The impeller assembly according to claim 14, wherein the polyhydroxyl compound has molecular weight from 500 to 4,000.

16. The impeller assembly according to claim 8, wherein the chain extender is a diamine selected from the group consisting of ethylenediamine, 1,3-diaminopropane, 1,4-diaminobutane, 1,5-diaminopentane, 1,6-diaminohexane, 1,7-diaminoheptane, 1,8-diaminooctane, 1,9-diaminononane, 1,10-diaminodecane, and 1,4-diaminocyclohexane.

17. The impeller assembly according to claim 8, wherein the chain extender is a diol selected from the group consisting of ethylene glycol, propylene glycol, 1,4-butanediol, 1,5-pentanediol, 1,6-hexanediol, 1,7-hepatnediol, 1,8-octanediol, 1,9-nonanediol, 1,10-decanediol, and 1,4-cyclohexanediol.

18. The impeller assembly according to claim 8, wherein the chain extender comprises a diol and a diamine.

19. The impeller assembly according to claim 1, wherein the housing comprises a shape memory alloy metallic mesh.

20. The impeller assembly according to claim 19, wherein the shape memory alloy is selected from the group consisting of nickel-titanium, copper-zinc, copper-zinc-aluminum, copper-aluminum-nickel, gold-cadmium, and combinations thereof.

21. The impeller assembly according to claim 20, wherein the shape memory alloy comprises nickel-titanium.

* * * * *